US006221401B1

(12) United States Patent
Zasadzinski et al.

(10) Patent No.: US 6,221,401 B1
(45) Date of Patent: Apr. 24, 2001

(54) BILAYER STRUCTURE WHICH ENCAPSULATES MULTIPLE CONTAINMENT UNITS AND USES THEREOF

(75) Inventors: Joseph Zasadzinski, Santa Barbara, CA (US); Scott Walker, Woodbury, MN (US); Michael Kennedy, Goleta, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/139,045

(22) Filed: Aug. 24, 1998

Related U.S. Application Data

(63) Continuation-in-part of application No. 08/980,332, filed on Nov. 28, 1997, now abandoned.
(60) Provisional application No. 60/032,306, filed on Dec. 2, 1996, now abandoned.

(51) Int. Cl.[7] ............................... A61K 9/14; A61K 9/16; A61K 9/50
(52) U.S. Cl. .................. 424/490; 424/423; 424/427; 424/430; 424/434; 424/435; 424/436; 424/444; 424/450; 424/489; 424/498; 514/821; 514/887; 514/966; 514/967; 514/968
(58) Field of Search .................... 424/450, 489, 424/490, 423, 427, 434, 435, 436, 430, 444, 498; 264/4.1, 4.3

(56) References Cited

U.S. PATENT DOCUMENTS

| 4,078,052 | 3/1978 | Papahadjopoulos | 424/36 |
|---|---|---|---|
| 5,004,566 | 4/1991 | Schnur et al. | 260/403 |
| 5,492,696 | 2/1996 | Price et al. | 424/417 |
| 5,576,017 | * 11/1996 | Kim | 424/450 |
| 5,618,560 | 4/1997 | Bar-Shalom et al. | 424/486 |
| 5,643,574 | 7/1997 | Gould-Fogerite et al. | 424/184.1 |
| 5,723,147 | * 3/1998 | Kim et al. | 424/450 |

OTHER PUBLICATIONS

Chiruvolu, Shivkumar et al., "Higher Order Self–Assembly of Vesicles by Site Specific Binding," *Science,* Jun. 17, 1994, 2364:1753–6. (Exhibit 6).
Papahadjopoulos, D. et al., "Effect of Proteins on Thermotropic Phase Transistors of Phospholipid Membranes," *Biochimica et Biophysica Acta,* 1975, 410:317–35. (Exhibit 7).
Papahadjopoulos, D. et al., "Cochleate Lipid Cylinders: Formation by Fusion of Unilamellar Lipid Vesciles," *Biochimica et Biophysica Acta,* 1975, 394:483–91. (Exhibit 8).
Papahadjopoulos, D. et al., "Induction of Fusion in Pure Phospholipid Membranes by Calcium Icons and Other Divalent Metals," *Biochimica et Biophysica Acta,* 1976, 448:265–83. (Exhibit 9).
Freireich, Emil J. et al., "Quantitative Comparison of Toxicity of Anticancer Agents in Mouse, Rat, Hamster, Dog, Monkey and Man," *Cancer Chemotherapy Reports,* May 1996, 50(4):219–44. (Exhibit 10).

* cited by examiner

*Primary Examiner*—James M. Spear
(74) *Attorney, Agent, or Firm*—Mandel & Adriano

(57) ABSTRACT

The present invention provides a bilayer structure for encapsulating multiple containment units. These containment units can attach or contain therapeutic or diagnostic agents that can be released through the bilayer structure. A suitable example of such a containment unit is a unilamellar or multilamellar vesicle.

27 Claims, 6 Drawing Sheets

BILAYER STRUCTURE WHICH ENCAPSULATES MULTIPLE CONTAINMENT UNITS AND USES THEREOF

This application is claiming the priority under 35 U.S.C. §119(e) of provisional application, U.S. Ser. No. 60/032,306, filed Dec. 2, 1996 and is a continuation in part application of U.S. Ser. No. 08/980,332, filed Nov. 28, 1997 now abandoned both of which are incorporated by reference.

This invention was made with Government support under NSF grant DMR-9123048, CTS9212790 and CTS9319447 and NIH grant GM47334. The Government has certain rights in this invention.

BACKGROUND OF THE INVENTION

Conventional drug delivery technology, which in the past has concentrated on improvements in mechanical devices such as implants or pumps to achieve more sustained release of drugs, is now advancing on a microscopic and even molecular level. Recombinant technology has produced a variety of new potential therapeutics in the form of peptides and proteins and these successes have spurred the search for newer and more appropriate delivery and targeting methods and vehicles.

Microencapsulation of drugs within biodegradable polymers and liposomes has achieved successes in improving the pharmacodynamics of a variety of drugs such as antibiotics and chemotherapeutic agents. For example, unilamellar vesicles are currently used as drug delivery vehicles for a number of compounds where slow, sustained release or targeted release to specific sites in the body are desired. The drug to be released is contained within the aqueous interior of the vesicle and release is achieved by slow permeation through the vesicle bilayer. A variety of modifications of the unilamellar vesicle membrane have been attempted, including polymerizing or crosslinking the molecules in the bilayer to enhance stability and reduce permeation rates, and incorporating polymers into the bilayer to reduce clearance by macrophages in the bloodstream.

One example of such a vesicle structure is known as Depofoam. Depofoam is a multivesicular particle that is created by multiple emulsification steps. A defined lipid composition is dissolved in a volatile solvent. The dispersed lipids in solvent are vigorously mixed with water to form a first emulsion, designated a solvent continuous emulsion.

This first emulsion is then added to a second water/solvent emulsion and emulsified to form a water in solvent in water double emulsion. The solvent is removed from the mixture resulting in discrete foam-like spherical structures consisting of bilayer separated water compartments. The minimum size of these structures is about 5–10 microns. Depofoam does not include a distinct bilayer structure that encapsulates the multivesicular particles, i.e., there are no individual, distinct interior vesicles. Therefore, the interior compartment must share bilayer walls.

Liposomes are sealed, usually spherical, either unilamellar or multilamellar vesicles which are capable of encapsulating a variety of drugs. Liposomes are the most widely studied vesicles to date and they can be formulated with a variety of lipid types and compositions that can alter their stability, pharmacokinetics and biodistribution. A major disadvantage of both multilamellar and unilamellar liposomes as delivery systems is their size, which prevents them from crossing most normal membrane barriers and limits their administration to the intravenous route. In addition, their tissue selectivity is limited to the reticuloendothelial cells, which recognize them as foreign microparticulates and then concentrates the liposomes in tissues such as the liver and spleen.

Polymers have also been used as drug delivery systems. They generally release drugs by (1) polymeric degradation or chemical cleavage of the drug from the polymer, (2) swelling of the polymer to release drugs trapped within the polymeric chains, (3) osmotic pressure effects, which create pores that release a drug which is dispersed within a polymeric network, and/or (4) simple diffusion of the drug from within the polymeric matrix to the surrounding medium.

With the success and drawbacks of these microencapsulation vehicles, today the challenge is to produce better and more efficient microencapsulation vehicles to enhance drug delivery. The present invention is directed to meeting that challenge.

SUMMARY OF THE INVENTION

The present invention provides a bilayer structure for encapsulating multiple containment units, e.g., polymer containment units. Containment units can attach or contain therapeutic or diagnostic agents that can be released through the bilayer structure. A suitable example of such a containment unit is a unilamellar or multilamellar vesicle.

The invention provides compositions comprising the bilayer structure of the invention and multiple containment units. Preferably, the containment units are aggregated.

In one embodiment of the invention, these compositions include vesosomes. Vesosomes have a bilayer structure that encapsulates multiple containment units in the form of vesicles. Generally, the multiple vesicles are aggregated. Vesicles can be unilamellar or multilamellar.

The vesicles can either be of similar size and composition or of varied size and composition. Preferably, each vesicle is attached to another (or aggregated) via ligand-receptor or antibody-antigen interactions.

Further, the encapsulating bilayer structure can attach to the aggregated vesicles via ligand-receptor interactions. By optimizing both the exterior bilayer structure and the interior vesicle compositions, the size and size distribution of the interior vesicles, the overall size of the vesosome, the nature of the attachments of the vesicles, and the type of additives to the outer bilayer (such as polymers or specific recognition sites), an extremely versatile drug delivery system can be developed for a variety of applications.

DETAILED DESCRIPTION OF THE INVENTION

DEFINITIONS

Figure 1:
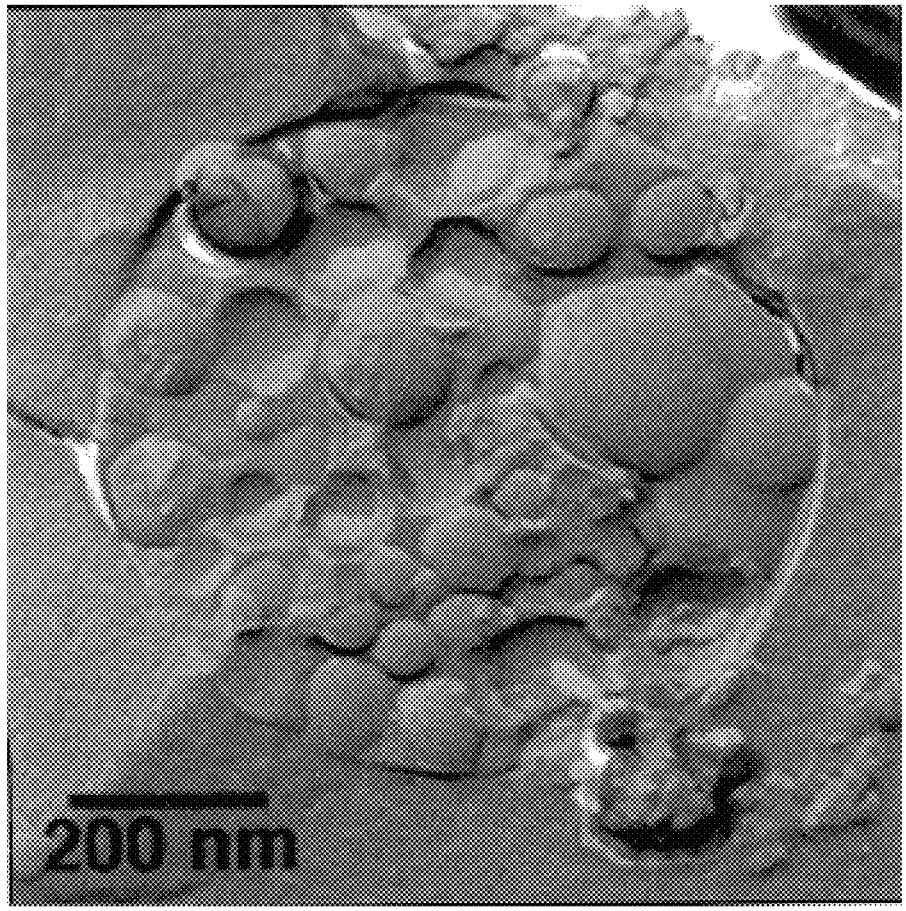
FIG. 1 is a freeze-fracture transmission electron micrograph of a typical vesosome prepared upon mixing cochleated cylinders with sized vesicle aggregates (at a 1:1 mole ratio) prior to the addition of EDTA. There is only one outer bilayer, and the interior vesicles appear to be specifically aggregated.

As used in this application, the following words or phrases have the meanings specified.

As used herein, the term "containment units" means any structure having space that can be occupied by an agent such as a therapeutic, diagnostic, or cosmetic agent. Typically, the structure is spherical but is not necessarily so.

As used herein the term "vesosome" is an aggregate of unilamellar or multilamellar vesicles encapsulated within a distinct bilayer structure. The interior vesicles can be of a single size and membrane or interior composition or number of layers, or of varied sizes and/or membrane or interior composition or number of layers. These parameters can be controlled during the assembly process described herein.

As used herein "uniform size" means of approximately similar size. It does not necessarily mean vesicles having an identical size.

In order that the invention herein described may be more fully understood, the following description is set forth.

COMPOSITIONS OF THE INVENTION

The invention provides a bilayer structure for encapsulating multiple containment units.

The present invention further provides a vesosome having the bilayer structure of the invention that encapsulates multiple vesicles. Generally, the vesicles are aggregated within the bilayer structure (S. Chiruvolu et al. (1994) Science 264:1753). The interior vesicles can be of a single size and membrane or interior composition, or of varied sizes and/or membrane or interior composition. The interior vesicles can either be unilamellar or multilamellar. These parameters can be determined during the assembly process described below. The total dimensions of the vesosome can be controlled from about 0.05 micron to >5 micron. The vesosome can incorporate a variety of water or lipid soluble drugs or other solutes within the interior vesicles, or within the exterior capsule, or both. These drugs can then permeate slowly through the interior and exterior bilayers, providing a controlled, slow release of drugs over time. Aggregation can be effected by ligand-receptor or antibody-antigen interactions. Other aggregation means are possible. The vesosome of the invention is submicroscopic in size. Further, in accordance with the practice of the invention, the multiple vesicles are of uniform size. Alternatively, the multiple vesicles are of dramatically different sizes.

METHODS FOR MAKING AND USING COMPOSITIONS OF THE INVENTION

The invention further provides a method for encapsulating multiple vesicles within an outer membrane. This method comprises obtaining aggregated multiple vesicles in a solution. Cochleated cylinders are then added to the solution [Papahadjopoulos, D., et al., (1974) *Biochim. Biophys. Acta*, 401, 317–335; Papahadjopoulos, D., et al., (1975) *Biochim. Biophys. Acta*, 394, 483–491; Papahadjopoulos, D., et al., (1976) *Biochim. Biophys. Acta*, 448, 265–283].

The aggregated vesicles and cochleated cylinders are mixed in the solution under suitable conditions so that the cochleated cylinders transform to create the bilayer structures of the invention which encapsulates the aggregated multiple vesicles.

In accordance with the practice of the invention, the interior vesicles can include a therapeutic agent. Alternatively, the interior vesicles can include a diagnostic agent. The interior vesicles can include a reactive agent, so as to create new compounds in situ. Methods for including agents within the containment units (e.g., vesicles) are well known because methods for including such agents into liposomes are well known (CA 1314209; DE 3880691; GB 9605915; DE 4402867).

Suitable therapeutic agents include, but are not limited to, the following.

The therapeutic agent can include antimicrobial agents such as antibiotics, antifungal, and antimycobacterial drugs. Examples of antibiotics include, but are not limited to, amikacin, kanamycin B, amphomycin, bacitracin, bicyclomycin, capreomycin, polymyxin E, cycloserine, chloramphenicol, dactinomycin, erythromycin, gentamicin, gramicidin A, penicillins, rifamycins, streptomycin, and tetracyclines.

The therapeutic agent can be a drug acting at synaptic and neuroeffector junctional sites. Examples include neurohumoral transmitters, cholinergic agonists, anticholinesterase agents, antimuscarinic drugs, agents acting at the neuromuscular junction and autonomic ganglia, catecholamines, sympathomimetic drugs, and adrenergic receptor antagonists.

Alternatively, the therapeutic agent can be a drug acting on the CNS. Examples include antipsychotic drugs, neuroleptic drugs, tricyclic antidepressants, monoamine oxidase inhibitors, lithium salts, and benzodiazepines.

Additionally, the therapeutic agent can be a drug that reduces inflammation. Examples include antagonists of histamine, bradykinin, 5-hydroxytryptamine; lipid-derived autacoids; methylxanthines, cromolyn sodium; and analgesic-antipyretics.

The therapeutic agent can be a drug that affects renal function and electrolyte metabolism. Examples include diuretics and inhibitors of tubular transport of organic compounds.

The therapeutic agent can be a drug that affects cardiovascular function. Examples include renin and angiotensin; organic nitrates, calcium-channel blockers and beta-adrenergic antagonists; antihypertensive agents, digitalis, antiarrhythmic drugs, and drugs used in the treatment of hyperlipoproteinemias.

Suitable diagnostic agents include, but are not limited to, radiolabels, enzymes, chromophores and fluorescers.

In accordance with the practice of the invention, the aggregated multiple vesicles of step (a) of the method and the cochleated cylinders of step (b) of the method can be mixed in a suitable ratio, e.g., a 1:1 ratio. Other ratios are possible.

The present invention provides a method for delivering a therapeutic agent to a wound site. This method comprises introducing the vesosome of the invention to the wound site. This is done under conditions so that the therapeutic agent is released from the vesosome to the wound site. Alternatively, the method also include delivering an agent to an intended site for cosmetic, veterinary, and other applications requiring slow release of a particular agent (CA 1314209; DE 3880691; GB 9605915; DE 4402867).

Introduction of the vesosome to the wound site can be effected by various methods. For example, the vesosome can be introduced by intramuscular injection, intravenous injection, oral administration, pulmonary adsorption, rectal administration, subcutaneous injection, sublingual administration, or topical application. Other methods and administration methods are possible and well known in the art.

The most effective mode of administration and dosage regimen for the molecules of the present invention depends upon the severity and course of the disease, the subject's health and response to treatment and the judgment of the treating physician. Accordingly, the dosages of the molecules should be titrated to the individual subject.

The interrelationship of dosages for animals of various sizes and species and humans based on mg/m² of surface area is described by Ferrite, E. J., et al. (Quantitative Comparison of Toxicity of Anticancer Agents in Mouse, Rat, Hamster, Dog, Monkey and Man. Cancer Chemother, Rep., 50, No.4, 219–244, May 1966).

Adjustments in the dosage regimen can be made to optimize the response. Doses can be divided and administered on a daily basis or the dose can be reduced proportionally depending upon the situation. For example, several divided doses can be administered daily or the dose can be proportionally reduced as indicated by the specific therapeutic situation.

The invention further provides a method for obtaining aggregated vesicles having a uniform size. As used herein, "uniform size" means having about the same, but not necessarily having identical, size.

This method comprises filtering aggregated vesicles having varying sizes through multiple membranes under pressure. By doing so, the vesicle aggregates so filtered have substantially uniform size. For example, the vesicles so extruded can have a size ranging from 0.05–5 μm.

The vesicles are filtered through two membranes, although this is not essential to the process. Generally, the membranes have filter pores of uniform size.

Possible Modifications and Variations

As mentioned, the detailed composition and size of the interior vesicles is not important to the process. Other types of vesicle preparation methods can be used, from (1) chemical preparations such as reverse phase evaporation, detergent dialysis, pH jump, (2) other mechanical treatments such as ultrasonication, and (3) spontaneous vesicle preparations which lead directly to equilibrium vesicles (without special treatments). Unencapsulated drug product can be removed at any stage of this process by various dialysis techniques, ion exchange, chromatography, filtration or centrifugation.

The aggregation of the vesicles can also be accomplished by a variety of ligand-receptor interactions, via antigen-antibody, or via chemical crosslinking agents that mimic ligand-receptor interactions.

Aggregate sizing can be accomplished by other methods such as (1) quenching the aggregation (adding another ligand that binds to the receptor, preventing it from cross-linking more vesicles), (2) using charged vesicles that will aggregate at a slower rate due to enhanced electrostatic repulsion between the vesicles and (3) altering the stoichiometric ratio of the ligand to receptor, which also can lead to a slower, controlled aggregation. Monodisperse aggregate sizes can be prepared by removing excess freely floating vesicles or small aggregates by various centrifugation or dialysis techniques. Finally, polymers such as polyethylene glycol linked to lipids can be incorporated into the exterior membrane to sterically stabilize the vesosome against aggregation and/or clearance by macrophages. The various processes can be optimized for a particular drug release or other application.

There are also different methods of forming the exterior membrane in addition to the method described above. The simplest and most general is to use a layer of large vesicles attached to the aggregated vesicles, then osmotically stress these exterior vesicles to "pop" them, thereby forming a continuous encapsulating membrane in the process. A second method is to use large, flaccid vesicles to engulf the aggregated vesicles in a type of endocytosis process, again mediated by ligand receptor or similar interactions.

Advantages of the Invention

The benefits of the vesosome over single walled vesicles used for drug delivery is that important membrane functions can be divided among two or more membranes rather than one. For example, the permeation rate, the membrane charge, specific recognition molecules, steric stabilizers, membrane rigidity and phase transition temperatures all play a role in the optimization of a drug delivery vehicle.

With the vesosome structure, these often incompatible attributes can be divided among the various membranes. The exterior membrane can incorporate steric stabilizer molecules such as polyethylene glycol, or specific recognition sites such as ligand or specific receptors. The interior vesicles can be made of various sizes and compositions to optimize the permeation of drugs from the vesosome. The interior vesicles within the vesosome can be of different composition or size from each other as well to optimize delivery of multiple drugs, or prolong delivery over time.

Building the vesosome takes advantage of several new features including:

1) Specific aggregation of vesicles via ligand-receptor interactions (Chiruvolu et al., 1994)
2) Sizing the vesicle aggregates via extrusion
3) Encapsulating the vesicles within a second membrane. As far as we have been able to determine from the scientific literature, this is the first time vesicles have been encapsulated within another bilayer by a controlled and reproducible process [Cevc, G. and Marsh, D. (1987) *Phospholipid Bilayers: Physical Principles and Models*, Wiley, N.Y.; Lasic, D. D. (1993) *Liposomes: From Physics to Applications*, Elsevier, Amsterdam].

The greatest benefit to this step-wise process of construction is the great flexibility it allows in optimizing bilayer composition, aggregate size, etc. Also, as many of the steps in the process are spontaneous self-assembly steps, they are especially simple and only involve mixing one or more solutions. As a result, these steps are quite efficient and easy to scale up.

The following example is presented to illustrate the present invention and to assist one of ordinary skill in making and using the same. The example is not intended in any way to otherwise limit the scope of the invention.

EXAMPLE 1

Figure 2:
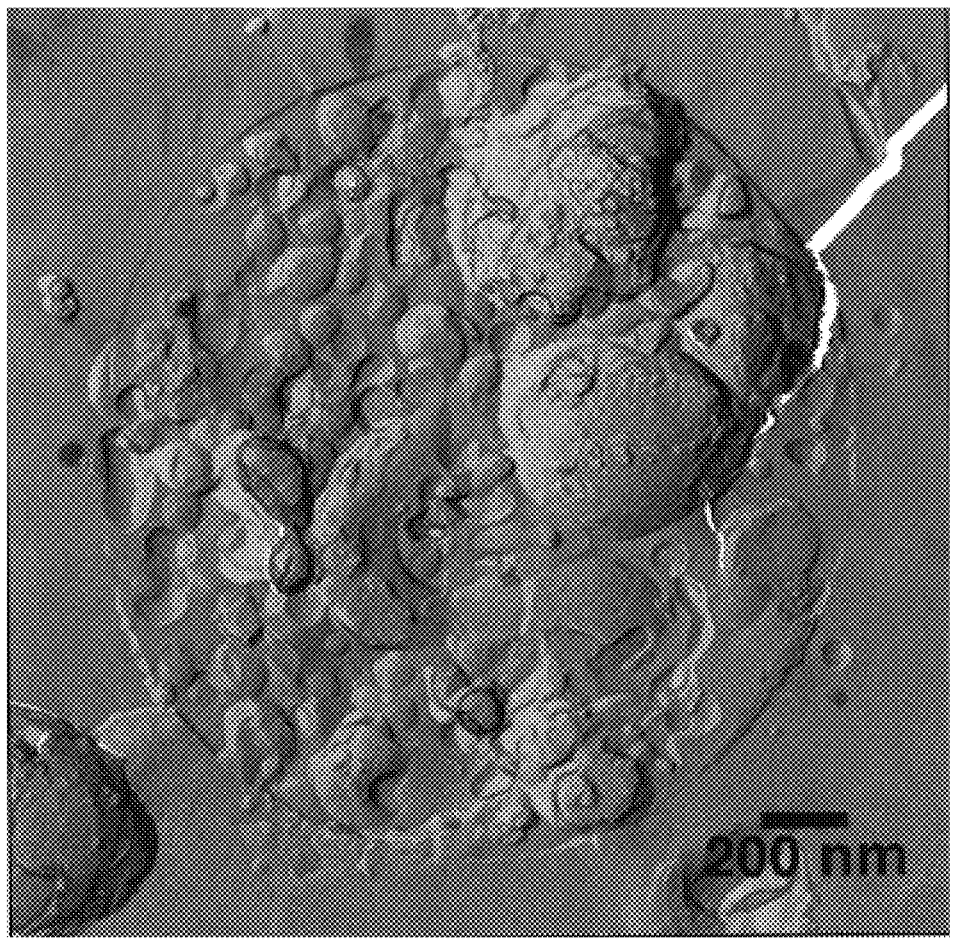
FIG. 2 is a freeze-fracture transmission electron micrograph of a typical vesosome prepared upon mixing cochleated cylinders with active sized aggregates (at a 1:1 mole ratio) after addition of EDTA. Again, there is only one outer bilayer, and the interior vesicles appear to be specifically aggregated. The two figures differ only in that EDTA has been added to the second sample to chelate the remaining calcium.
Figure 3:
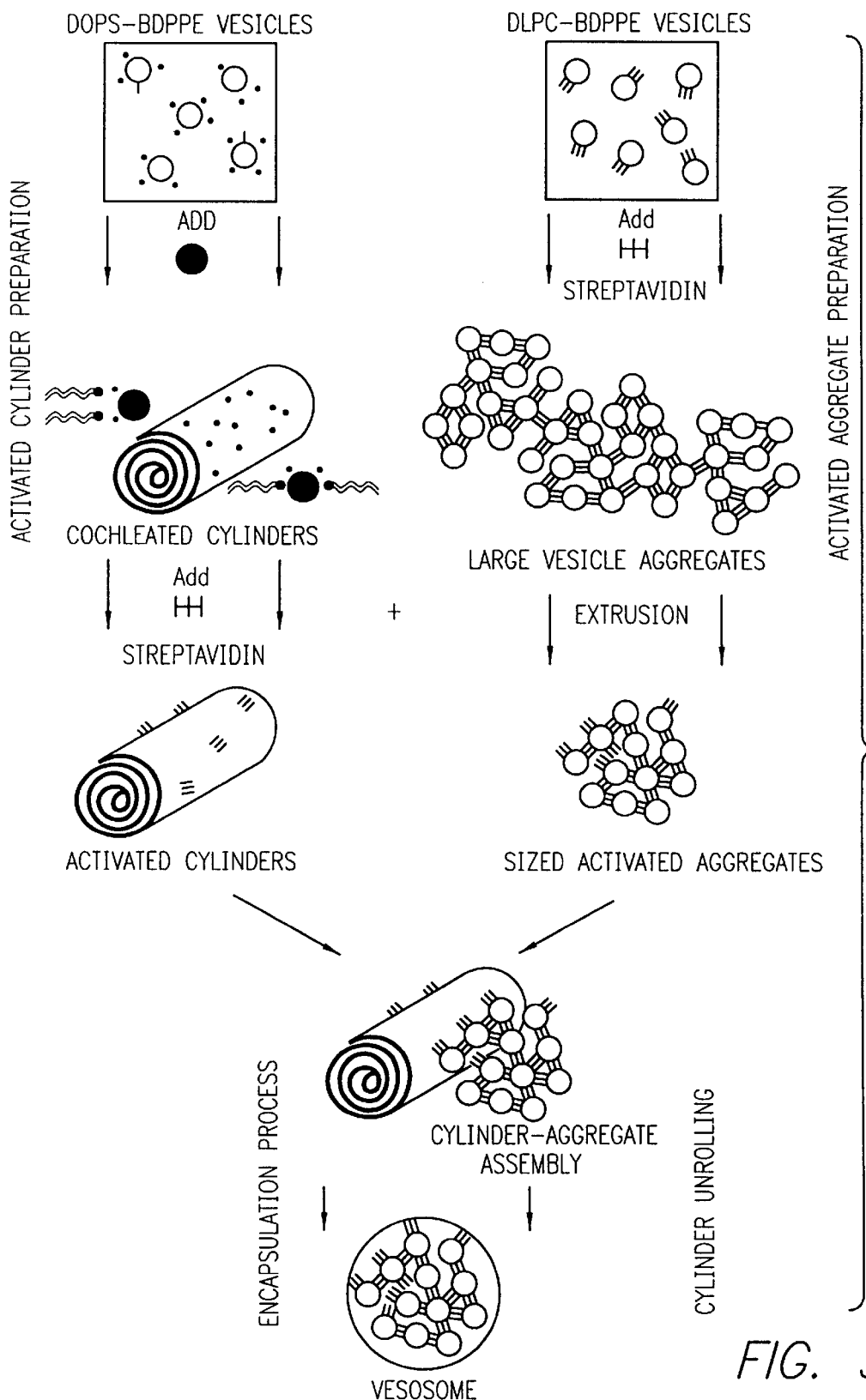
FIG. 3 is a schematic representation of one embodiment for vesosome production.
Figure 5:
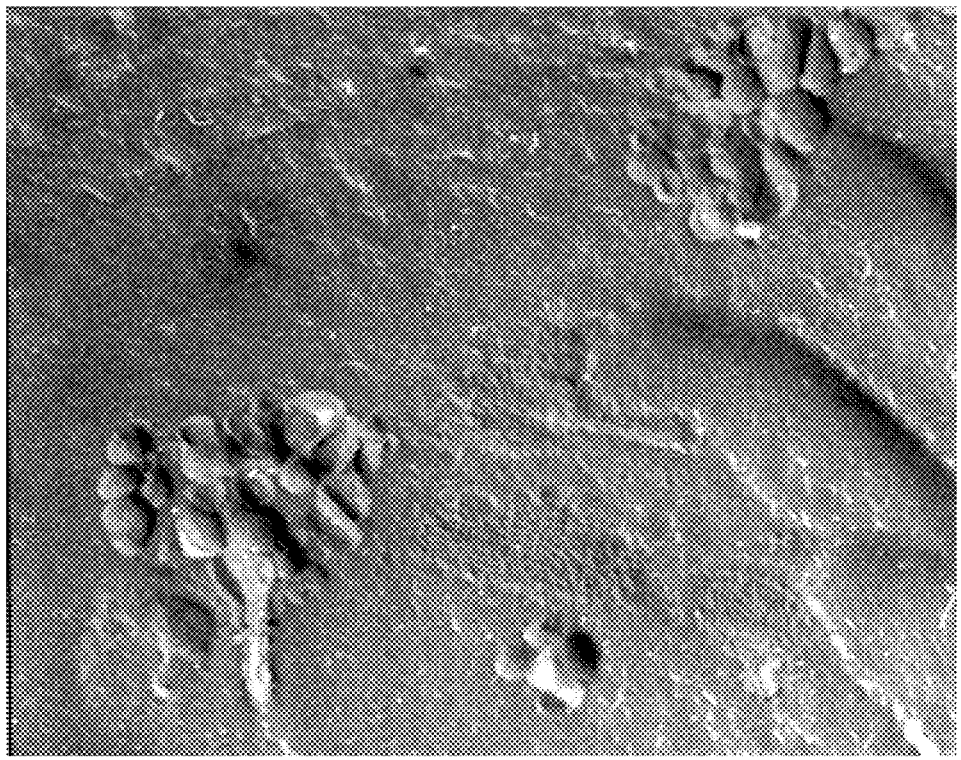
FIG. 5 is a photograph showing stable, small aggregates formed by adding streptavidin to biotin-labeled vesicles at a ratio of about 2 surface accessible biotins to streptavidin, this corresponds to a total mole ratio of about 4 biotins per streptavidin.

In this example, the preparation of a vesosome is essentially a two-step process (FIGS. 3 and 5). The first step is creating a controlled-size vesicle aggregate. The second step is encapsulating the vesicle aggregate within an outer membrane. Here we provide a specific example of the techniques used to create the vesosomes shown in FIGS. 1 and 2 above. In each case, the specifics of the lipids and crosslinking agents, the size distributions, etc., used are only representative and can be optimized to suit the application.

Vesicle Preparation:

The vesicles can be made from a variety of phospholipids, cholesterol, fatty acids, etc. as needed. To create the vesosomes shown in FIGS. 1 and 2, 150 mg of dilauroylphosphatidylcholine (DLPC) (Avanti Polar Lipids, Alabaster, Ala.) and 0.4 mg of biotin-X-dipalmitoylphosphatidylethanolamine (B-DPPE) (Molecular Probes, Eugene, Oreg.) were mixed together in a 2 dram sample vial in chloroform (the B-DPPE was present at 0.163 mole % of total lipid in solution) to thoroughly mix the lipids. The chloroform was removed by evaporation under vacuum. 5 mL of aqueous buffer/salt/azide solution (100 mM NaCl, 50 mM TES, and 0.02 wt % $NaN_3$ balanced to pH 7.2) was added to the dried lipid to create a solution of 30 mg/mL total lipid. The sodium azide is used as a preservative, and is not necessary for the process.

After fully hydrating the lipids, the resultant solution consisted of multilamellar vesicles (MLVs). Unilamellar vesicles were formed from the MLV's by a mechanical extrusion technique [Mayer, E. (1985) *J. Microsc.* 140, 3–15]. The MLV solution was repeatedly (1) frozen in a liquid nitrogen (T=–190° C.) bath for 30–60 seconds, then (2) immediately melted in a 50–60° C. water bath. This process disrupts the multilamellar structure of the vesicles and leads to the formation of large unilamellar vesicles (LUVs; polydisperse, up to a few microns in size). The solution is then allowed to cool to room temperature (25° C.). The LUV suspension is then put through 8–12 high pressure (approximately 50 psi dry nitrogen) extrusion cycles by filtering the solution within an Extruder (Lipex Biomembranes, Vancouver, BC, Canada) through two stacked Nuclepore filters of pore diameter 0.1 $\mu$m. This process produces a 30 mg/mL monodisperse population of unilamellar vesicles (ULVs) approximately 100 nm in diameter. These vesicles consist of DLPC and B-DPPE, with B-DPPE being present in the bilayer at 0.163 mole %. The biotin ligand is oriented away from the bilayer (in the same direction as the headgroups). This creates a vesicle which has several ligands protruding from the both the interior and exterior surface. This solution of vesicles is then allowed to equilibrate for at least a few hours. Although metastable, these ULVs remain freely suspended for several weeks without reverting to their equilibrium MLV structure.

Vesicle Aggregate Preparation:

To aggregate the vesicles, an aqueous dispersion of streptavidin molecules (mol. wt. 60,000 g/mol) in the same buffer solution is added to the extruded vesicles. In this example, 3.94 mg of streptavidin (Molecular Probes, Eugene, Oreg.) is measured and mixed with 6.24 mL of the TES/NaCl/azide buffer solution to create a 0.63 mg/mL streptavidin solution. 1.0 mL of streptavidin solution is added to a vial containing 2.0 mL of the DLPC/B-DPPE ULV suspension. The overall biotin-streptavidin mole ratio for this system is about 15:1, however, the ratio of exposed biotin (biotins on the outer vesicle monolayer) to streptavidin is about 8:1. Since there are four identical binding sites of streptavidin available for binding, the ratio of exposed biotins to binding sites is 2:1. Within an hour, the 20 mg/mL ULV/streptavidin suspension changes color from clear and bluish to opaque and cloudy, indicating that much larger particles are being formed, i.e., the vesicles are aggregating. This vesicle aggregation scheme does not appear to stress or rupture the individual vesicles. This process was developed in our laboratory [Chiruvolu, S., et al., (1994) *Science* 264, 1753–1756].

Controlled-Size Vesicle Aggregates Preparation:

Vesicle aggregate sizing is done by extruding the large vesicle aggregates through two stacked Nuclepore filters of pore diameter 1.0 $\mu$m; this extrusion is essentially identical to the extrusion step in ULV production, except the pore size is larger. This produces a dispersion of vesicle aggregates with sizes ranging from 0.3–1.0 $\mu$m. Once formed, the sized vesicle aggregates are stable for weeks and experience minimal re-aggregation or re-dispersion.

Encapsulating Sized Aggregates

To encapsulate the vesicle aggregate, we take advantage of microstructures common to negatively charged lipids in the presence of calcium ions. Cochleated cylinders are multilamellar lipid tubules formed spontaneously by certain negatively charged phospholipids in the presence of calcium ions. $Ca^{2+}$ is known to induce the adhesion, fusion and collapse of bilayers containing large proportions of the anionic phospholipid phosphatidylserine (PS) [Papahadjopoulos, D., et al., (1974) *Biochim. Biophys. Acta*, 401, 317–335; Papahadjopoulos, D., et al., (1975) *Biochim. Biophys. Acta*, 394, 483–491; Papahadjopoulos, D., et al., (1976) *Biochim. Biophys. Acta*, 448, 265–283]. These dehydrated multilamellar structures have been synthesized in our laboratory using similar techniques reported in the literature as discussed below. We have independently confirmed the presence of cochleated cylinders in our experiments by FF-TEM.

DOPS, Unilamellar Vesicle Preparation:

Vesicles, composed of 1,2 dioleoylphosphatidylserine (DOPS; AVANTI Polar Lipids, Inc., Alabaster, Ala.) and containing small amounts of B-DPPE (Molecular Probes, Inc., Eugene, Oreg.) were made as precursors to cochleated cylinders through similar methods as described above.

Briefly, 50 mg of lyophilized DOPS (61.7 $\mu$moles) was dissolved in 5 mL of Chloroform with 0.1 ml of B-DPPE solution [$9.8 \times 10^{-8}$ mole B-DPPE] to give a mole fraction of B-DPPE of 0.0016. The chloroform was evaporated under dry nitrogen and the lipid vacuum dried to remove excess solvent. The dried, mixed lipids were then hydrated (or resuspended) in 5 mL aqueous buffer solution as described above, yielding a solution with DOPS (MW 810 g/mol) concentration of 10 mg/mL (12.3 mM) and a B-DPPE (MW 1019 g/mol) concentration of 0.02 mg/mL (0.02 mM).

After dispersing the lipid by vortexing, we allowed equilibration of the solution at 37° C. for 24 hours. The multilamellar vesicle solution was taken through several freeze-thaw cycles prior to sizing by high pressure extrusion through Nuclepore 0.1 $\mu$m polycarbonate membranes. The sized vesicles were allowed to equilibrate at 25° C. prior to the addition of $Ca^{2+}$.

$Ca^{2+}$ Solution Preparation:

Solutions containing millimolar quantities of free $Ca^{2+}$ were prepared using anhydrous $CaCl_2$ salt (Sigma Chemical Co., St. Louis, Mo.) and the standard buffer solution. Previous experiments by our laboratory revealed that the concentration of $Ca^{2+}$ in solution required to induce fusion between small unilamellar vesicles of DOPS be greater than 2.0 mM. A 6.0 mM $CaCl_2$ buffer solution was prepared for use in these experiments.

Cochleated Cylinders Preparation:

Equal 1 mL volumes of the DOPS/B-DPPE vesicle solution (10 mg/mL) and the 6 mM $CaCl_2$ buffer solution were measured using two 1000 $\mu$L Hamilton Gas-Tight™ syringes. The two solutions were simultaneously dispensed into a clean, dry 3-dram vial, where they rapidly mixed to form a solution with a DOPS concentration of 5 mg/mL (6.2 mM), a B-DPPE concentration of 0.01 mg/mL (0.01 mM) and a $CaCl_2$ concentration of 3 mM.

Immediately upon mixing, the turbidity of the solution increased. Aggregation, fusion and collapse of the DOPS/B-DPPE vesicles—and transition into cochleated cylinders—began immediately.

Streptavidin (Molecular Probes, Inc., Eugene Oreg.) was dissolved in the standard buffer for a solution with a concentration 0.63 mg/mL ($1.0 \times 10^{-8}$ mol/mL). 35 $\mu$L of the streptavidin solution was injected into 1 mL of the cochleated cylinder solution to activate the cylinders. The product was gently mixed and allowed to equilibrate for 24 hours.

Vesosome Preparation:

We have now described how to prepare the two precursor solutions (in identical buffers) needed for vesosome production. First, we have a solution of active vesicle aggregates (with some active freely floating vesicles). Second, we have a solution of active cochleated cylinders (with likely some freely floating streptavidin).

We have employed two different mixing ratios of the two precursor solutions that produce the vesosome solutions. To briefly describe, one mixture is prepared such that the ratio of the number of moles of DLPC lipids to DOPS lipids equals one. The second mixture is prepared such that the ratio of the approximate number of sized vesicle aggregates (taking into account the freely floating vesicles) to the approximate number of cochleated cylinders equals one. In the latter case, we are attempting to match at least one aggregate with one cylinder. In the former case, we are ensuring that there are plenty of aggregates to get encapsulated.

In the mole-match case, 1.0 mL of the 5 mg/mL (DOPS) active cochleated cylinders/streptavidin solution is added to the 20 mg/mL (DLPC) 0.190 mL of active sized vesicle aggregates simultaneously. That is, 6.2 μmol of DOPS molecules is mixed with 6.2 μmol of DLPC molecules. Upon mixing, the solution turned from chunky, crystal-like structures consistent with suspensions of cylinder solutions to more opaque and less chunky.

In the number-match case, 1.0 mL of the 5 mg/mL (DOPS) active cochleated cylinders/streptavidin solution is added to the 20 mg/mL (DLPC) 0.040 mL of active sized vesicle aggregates simultaneously. That is, 6.2 μmol of DOPS molecules is mixed with 1.3 μmol of DLPC molecules. Therefore, in the mole-match case, there are about 5 times as many aggregates as in the number-match case. Again, upon mixing, the nature of the solution changed.

Freeze-fracture TEM Results

Aliquots for freeze-fracture sample preparation were taken from both the mole-match and number-match solutions one day after mixing the cylinders and aggregates.

In general, FF-TEM revealed that most of the structures present in either the mole-matched or number-matched solution were LUVs (1–5 μm). Very few cylinders were observed. There did appear to be some unencapsulated sized aggregates as well a high concentration of free vesicles (100 nm). Actual concentrations or numbers are not available.

There did exist several vesosomes, as shown in FIG. 1. The interior aggregated vesicles (1) do appear to resemble the aggregated vesicles in both size (~0.5 μm) and aggregation state (dense and compact) prior to mixing the solutions and (2) are approximately 100 nm in size. These features indicate that the vesicles are indeed the DLPC vesicles and not DOPS vesicles which have managed to remain even after $Ca^{2+}$ addition.

There are, however, a few larger vesicles present within, and these may simply be larger DLPC ULVs or ULVs that have been formed by the fusion of several DLPC ULVs.

Also, note that the vesosome has a single bilayer encapsulating the entire vesicle aggregate, consistent with the "unrolling" of a cylinder.

A general encapsulation process could occur as follows: after mixing the solutions, an active aggregate approaches an active cylinder and binds to its surface by at least one biotin-streptavidin interaction. The aggregate proceeds to bind in several places until the binding force overcomes the force necessary to keep the cylinder wound. As the cylinder begins to unwind, the interior regions of the cylinder, now exposed to the aqueous solution, continue to bind around the aggregate until the cylinder unravels completely around the aggregate as if forced by the presence of EDTA.

Next, 0.44 mL of 5 mM EDTA solution (in the same buffer) was added to 0.5 mL of the mole-matched cylinder-aggregate mixture. The cloudy, opaque solution immediately turned grayish and more transparent. This cylinder-aggregate mixture consisted of approximately 4.2 mg/mL DOPS (cylinders) and 3.2 mg/mL DLPC (aggregates). The amount of EDTA added was in excess of the amount necessary to completely bind all of the available calcium ions and therefore cause unraveling of the cylinders. Also, 0.5 mL of the 5 mM EDTA solution was added to the number-matched mixture. Again, the solution changed to grayish and transparent. This number-matched mixture consisted of 4.8 mg/mL DOPS and 0.8 mg/mL DLPC. Again, excess EDTA was added. Aliquots of each of these solutions were also taken after approximately five hours of incubation for freeze-fracture sample preparation.

FF-TEM again revealed that each of these solutions contained very many LUVs (1–5 μm), as is expected in solutions in which EDTA has been added to cylinders. Also, there were several ULVs but no cylinders.

Vesosomes again were present in the number-match solution. FIG. 2 shows a typical vesosome seen in these solutions. Note, again, that interior vesicles appear to be aggregated as in the precursor solutions. However, there are also some very large vesicles, probably unraveled DOPS vesicles, which have become encapsulated as well. The number of vesosomes relative to the number of LUVs in these solutions does not seem to vary between the pre- and post-EDTA solutions, however, there seem to be more of them in the mole-matched solutions. This may indicate that the more active particles added to solution increases the chances for a vesosome to form.

It should be noted that the vesosome structures were not present in either of the precursor solutions. The solutions of cylinders saturated with streptavidin did not show any unusual characteristics due to the presence of the streptavidin; in fact, the cylinders seemed to become more dispersed, which may have been due to the bound streptavidin acting like a steric stabilizer, keeping the cylinders isolated from each other. The solutions of sized vesicles also did not exhibit any feature resembling a vesosome. No LUVs were even present in these solutions.

EXAMPLE 2

A simple, one step process was developed to produce colloidal aggregates with a well defined size distribution by controlling the ratio of reactive groups on the surface of the colloids (typically ligands such as a biotin coupled to a phospholipid incorporated in a vesicle membrane) to crosslinking agents (typically soluble biological receptors such as avidin or streptavidin) in solution. Other chemical ligands associated with the colloidal particles, and covalent crosslinking agents would also work as well. At a proscribed ratio of ligand to receptor, the receptor or crosslinker eventually saturates the ligands at the colloid surface, thereby limiting the aggregation process. This limited aggregation process is initiated by simple mixing of the ligand-labeled colloidal particles with the crosslinking agent or receptor. The crosslinking agent in solution competes for the limited number of surface ligands with ligands on other colloidal particles.

By having an excess of crosslinking agent, the ligands are eventually exhausted, and aggregation ceases when all of the ligands are coupled to a crosslinker. The process requires no specific mechanical or physical steps to initiate or limit the aggregation—aggregation proceeds by diffusion and reaction of the ligands and crosslinkers until equilibrium (at least metastable equilibrium) is reached. A mathematical model of the process was also developed that is consistent with experiment and shows a well defined transition between complete flocculation and limited aggregation that depends primarily on the ratio of crosslinker to surface ligands. This process can be generalized to any system of colloidal particles with surface accessible, reactive groups that could be coupled by a crosslinking agent.

The specific purpose of this embodiment is to have a one step method of producing vesicle aggregates of a limited size or aggregation number for use in making the vesosome drug delivery system (S. A. Walker et al., 1997). "Vesosomes" comprise a sized aggregate of unilamellar vesicles attached to each other via ligand-receptor interactions, encapsulated in a second bilayer, also attached via ligand-receptor interactions (See FIG. 1). The interior vesicles can be of a single size and membrane or interior composition, or of varied sizes and/or membrane or interior composition. The exterior membrane may also be of different composition, and may incorporate specific recognition or steric stabilization molecules on the surface.

For example, the total dimensions of a vesosome can be controlled from about 0.1 micron to >1 micron. The vesosome can incorporate a variety of water or lipid soluble drugs within the interior vesicles, or within the exterior capsule, or both. These drugs can then permeate slowly through the interior and exterior bilayers, providing a controlled, slow release of drugs over time.

The one step process aggregation process replaces a more complex, multistep process that involve complete flocculation of the vesicles followed by mechanical sizing via extrusion of the aggregated vesicles through filters of defined size (S. A. Walker et al., 1997).

This process does not put any stress on the vesicles as they aggregate nor does it require any additional filtering or purification steps as in the previous process. The filtering process also results in debris from destroyed vesicles and aggregates that needs to be removed prior to subsequent processing steps. Moreover, the surfaces of these limited aggregates are saturated by the crosslinking agent, hence the size distribution of the aggregates is stable for extended periods of time. The entire process is completed in a few minutes and requires no subsequent separations or purifications. The end result is a population of well defined aggregates with surfaces saturated by streptavidin, avidin, or whatever crosslinking agent was used.

This process can be used much more generally to create a larger colloidal aggregate from small particles. The process is independent of the details of the colloidal particles, crosslinking agent, or surface associated ligand. Prior to this work, non-specific colloidal aggregation induced by attractive interactions between the particles could not typically be controlled, other than to completely inhibit aggregation by making the interaction between colloidal particles sufficiently repulsive. As discussed in detail in the later sections, once colloidal aggregation was initiated, the aggregates would grow indefinitely and irreversibly. One of the only ways available to limit coagulation of liquid colloidal droplets was to use a surface active compound that could change the interaction between the colloidal droplets as a function of surface coverage.

In what is generally referred to as limited coalescence, a fine emulsion of liquid droplets is generated whose surface area is much larger than can be completely covered by a surface stabilizing agent. These small droplets are unstable to coalescence and grow, with a concomitant reduction in total interfacial area, until the stabilizing agent covers the interface at a sufficient level to halt further coalescence (T. H. Whitesides and Ross (1995)).

The ideal construction process for a sub-micron bilayer based drug delivery system includes a series of equilibrium "self-assembly" steps that require only simple mixing and minimal equipment and minimal purification. The main benefit of this new embodiment is to increase the speed and efficiency of vesosome construction through (1) optimizing the vesicle aggregation process by creating a self-limiting, one-step aggregation process by controlling the ratio of streptavidin to biotin and the total vesicle concentration described by theoretical models of self-limiting vesicle aggregation. FIG. 1 shows an electron micrograph of a vesosome constructed of 0.1 micron diameter dilaurylphosphatidylcholine interior vesicles aggregated via biotinated lipids and streptavidin, encapsulated in a dioleoylphosphatidylserine bilayer, also coupled to the aggregate with the biotinated lipid—streptavidin linkage. The overall dimensions of the vesosome is about 0.5 microns. Increasing the efficiency of vesosome production is a first step toward testing specific drug applications.

VESOSOME "CONSTRUCTION"

The vesosome can be designed to be sub-microscopic in size, with the interior vesicles ranging from, for example, 20–100 nm, and the entire aggregate from 0.1 to about 1 micron in diameter. FIG. 1 shows that the vesosome contains aggregated, spherical, unilamellar vesicles surrounded by an exterior membrane. The exterior membrane is continuous around the aggregated vesicles and the size distribution is consistent with that expected from the process described below.

The preparation of the vesosome is essentially a three-step process. The first step is making the interior vesicles and loading the specific drug to be delivered. These steps have been well worked out in the literature (T. M. Allen et al., 1995; T. M. Allen, 1996; D. D. Lasic, 1993; D. D. Lasic et al., 1996). The second step is creating a controlled-size vesicle aggregate, without disrupting the vesicle bilayer or contents. The third step is encapsulating the vesicle aggregate within an outer membrane.

Figure 4:
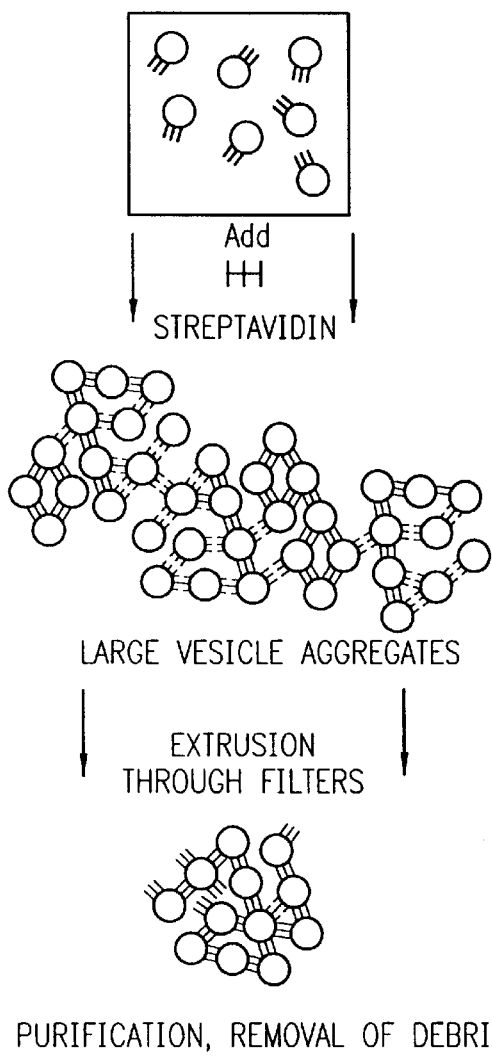
FIG. 4 is a schematic diagram of the processes set forth Examples 1 and 2.
Figure 4:
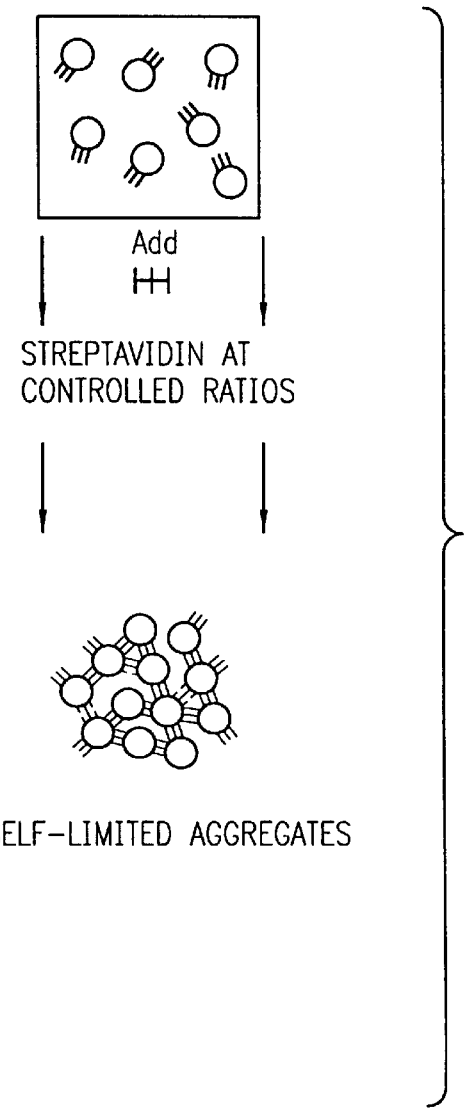

FIG. 4 shows the process for creating a controlled size vesicle aggregate in Example 1 and an additional embodiment of "self-limiting" aggregation in this Example. In the process of Example 1, biotin-labeled vesicles were added to streptavidin solution, leading to complete flocculation of the vesicles via biotin-streptavidin-biotin crosslinks. These flocculated vesicles were then reduced in size mechanically by extrusion through filters of a given pore size. This step was followed by purification of the extrudate to remove debris and disrupted vesicles.

In the process of Example 2, a controlled ratio of streptavidin or avidin is added to the biotin labeled vesicles (or any crosslinking agents), leading to aggregates of controlled size in a single mixing step. No mechanical sizing is needed. The process of Example 2 provides for the creation of aggregates that streamline vesosome production, eliminates time consuming mechanical filtration, separation, and extrusion steps, and helps to make the entire vesosome construction a simple series of controlled self-assemblies. These additional self-assembly tools of self-limiting aggregation should also have applications well beyond vesosome production.

A New Self-Limiting Colloidal Aggregation Process

In the process of Example 1, as shown in FIG. 4, sufficient streptavidin (Molecular Probes, Eugene, Oreg.) in buffer was added to vesicles containing a small fraction of biotin-lipid (Biotin-X—DPPE, Molecular Probes) to produce an overall streptavidin to biotin-lipid ratio of 1:15; however, the ratio of streptavidin to biotin-lipid on the outside of the vesicle available for binding was approximately 1:8. The remainder of the vesicle bilayer composition could be varied between pure dioleoylphosphatidylcholine to mixtures of distearoylphosphatidylcholine and cholesterol and did not affect the results of the aggregation process. As streptavidin has four distinct binding sites for biotin, the ratio of streptavidin binding sites to exposed biotin was 1:2, meaning there are always unreacted biotin-lipids. Within an hour after adding the streptavidin to the vesicle solution, the suspension changed from clear and bluish to opaque and cloudy-white, indicating that vesicle aggregates were forming. Aggregation continued indefinitely, producing multi-micron sized aggregates that eventually flocculated (S. A. Walker et al., 1997; T. H. Whitesides et al., 1995; T. M. Allen et al., 1995; T. M. Allen, 1996; D. D. Lasic, 1993; D. D. Lasic et al., 1996; S. Chiruvolu et al., 1994). However, aggregates for intravenous use must be of order 0.2–0.5 microns to facilitate long circulation times (with steric stabilization by PEG-lipid (T. M. Allen, 1996; D. D. Lasic, 1993; D. D. Lasic et al., 1996)). In the process of Example 1, the large vesicle aggregates were extruded through two stacked Nuclepore filters of pore size 1 $\mu$m. This produced a dispersion of vesicle aggregates with sizes ranging from 0.3–1.0 $\mu$m. The result that was that there was a large fraction of isolated vesicles and much smaller aggregates that would have to be removed at this step.

A simple, one-step, self-limiting aggregation process could significantly increase both the efficiency and speed of vesosome construction. However, colloidal aggregation is typically an all or nothing process when the interactions leading to the aggregation are attractive, but non-specific. However, we have found that if we increase the ratio of streptavidin to biotin so that there is roughly two biotin lipid sites available on the vesicle surface per streptavidin added (1:2) (experimentally, this corresponds to an initial mole ratio of roughly 4 biotin lipids per streptavidin, as half of the biotins point toward the interior of the vesicles, where they are not available for cross-linking), the aggregation process appears to be self-limiting. That is, the aggregation process stops with finite sized aggregates that are stable (See FIG. 5).

Modified Smolukowski Equation for Aggregation

In the original process described in Example 1 (S. A. Walker et al., 1997; T. H. Whitesides et al., 1995; T. M. Allen et al., 1995; T. M. Allen, 1996; D. D. Lasic, 1993; D. D. Lasic et al., 1996; S. Chiruvolu et al., 1994), vesicles (0.1 micron diameter) incorporating a small fraction of biotin-lipid could be completely aggregated when sufficient streptavidin or avidin (Molecular Probes) was added to produce a streptavidin to exposed biotin-lipid mole ratio, R, of approximately 1:8.

Titration of vesicles incorporating 0.16 mol % of biotin-X DHPE with fluorescent BODIPY-labeled avidin or streptavidin (Molecular Probes, Eugene, Oreg.) showed that the fluorescence intensity increased linearly up to a streptavidin to total biotin-lipid mole ratio between 1:8 and 1:9 at which the fluorescence saturated. As streptavidin has 4 binding sites per molecule, this shows that roughly one half of the total biotin-lipids were exposed on the outside of the vesicle. This is consistent with the expected complete miscibility of the biotin-X DHPE with the vesicle phospholipids.

As streptavidin (or avidin) has four distinct binding sites for biotin, there were always unreacted biotin-lipids exposed on the vesicle surface. Within a few minutes after adding the streptavidin to the vesicle solution, the suspension changed from clear and bluish to opaque and cloudy-white, indicating that vesicle aggregates were forming. Aggregation continued indefinitely, producing multi-micron sized aggregates that flocculated (S. A. Walker et al., 1997; T. H. Whitesides et al., 1995; T. M. Allen et al., 1995; T. M. Allen, 1996; D. D. Lasic, 1993; D. D. Lasic et al., 1996; S. Chiruvolu et al., 1994) (FIG. 6).

Figure 6:
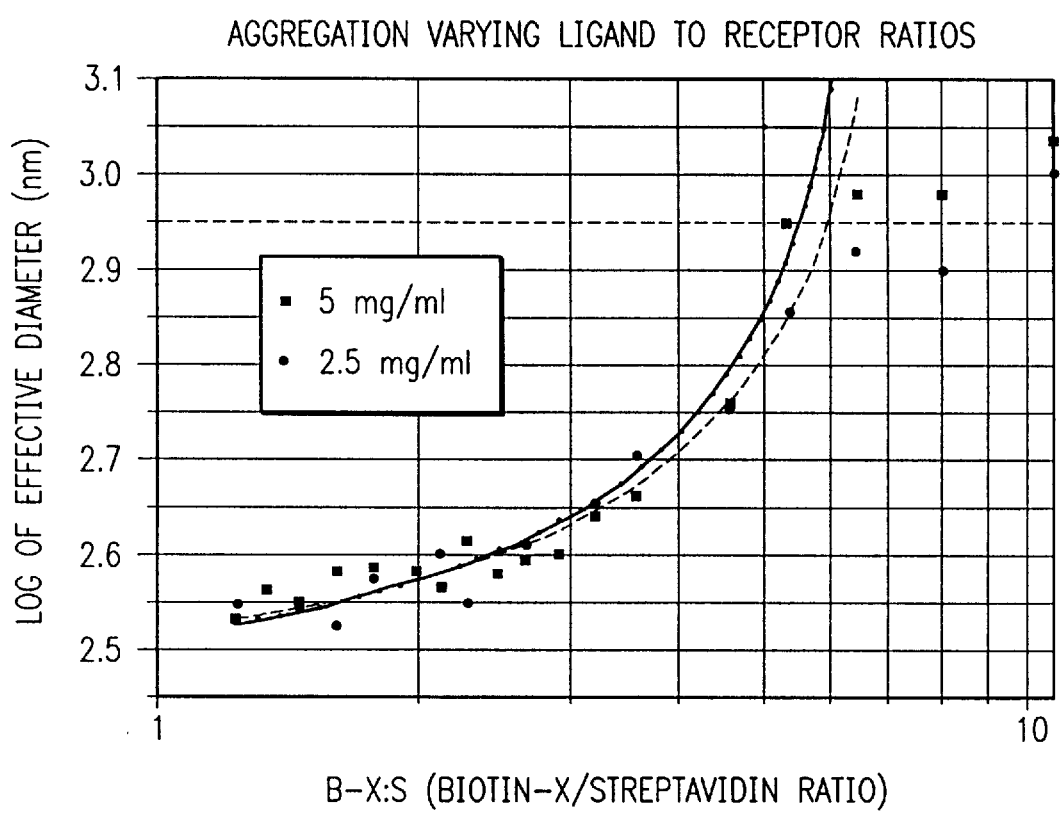
FIG. 6 is a line graph showing that vesicle aggregation and production continued indefinitely, producing multi-micron sized aggregates that flocculated.

However, as the ratio, R, of streptavidin to exposed biotin-lipid was increased to one streptavidin to less than four biotin-lipids available on the vesicle surface (R≦1:4), aggregation began to diminish as shown by dynamic light (DLS) scattering (FIG. 6). As the streptavidin to exposed biotin-lipid ratio was further decreased, (R≧1:2) flocculation ceased and DLS showed a dramatic decrease in the average aggregate size. This was confirmed by freeze-fracture electron microscopy (J. A. Zasadzinski et al., 1989) that showed a stable distribution of aggregates about 0.5 microns in diameter formed from the 0.1 micron diameter vesicles (FIG. 5). For larger values of R, the extent of aggregation did not change appreciably with R. No significant deformation of the vesicles occurred during any of the aggregation processes as shown by similar releases of entrapped carboxyfluorescein dye from aggregated and unaggregated vesicles.

While previous experiments showed that excess biotin-lipid led to complete aggregation (S. A. Walker et al., 1997; T. H. Whitesides et al., 1995; T. M. Allen et al., 1995; T. M. Allen, 1996; D. D. Lasic, 1993; D. D. Lasic et al., 1996; S. Chiruvolu et al., 1994), and a large excess of streptavidin led to very limited aggregation (H. C. Loughrey et al., 1990), the dramatic transition with receptor-ligand ratio was surprising. Vesicles aggregate by coupling a biotin-lipid on one vesicle to a streptavidin bound to a biotin-lipid on a second vesicle. The initial step in this process is the binding of a streptavidin in solution to the biotin lipid on a given vesicle. A competition for available biotin sites is set up between free streptavidin in solution and streptavidin already bound to another vesicle. Hence, the aggregation process is both initiated and inhibited by free receptor in solution. Sufficient streptavidin in solution eventually leads to the saturation of the ligands on the surface of the growing aggregate. Once all of the biotin-lipid sites on the growing vesicle aggregates are saturated with streptavidin, aggregation ends, leaving finite sized aggregates.

The classical description of rapid aggregation of colloidal particles is given by the Smolukowski equation, which has been shown to give reasonable agreement with experiment for non-specific diffusion-controlled colloidal aggregation (D. F. Evans et al., 1994). The Smolukowski equation gives the diffusion controlled rate of production of aggregates of size j and concentration [$P_j$] from smaller aggregates (i<j), less the consumption of aggregates of size j by further aggregation with any other aggregate. The rate constant, k is given by the mutual diffusion of the particles toward each other and is assumed to be constant, independent of the size of the particles or the aggregates:

$$d[P_j]/dt = k\left[1/2\sum_{i>j}[P_i][P_{j-i}], -[P_j]\sum_i[P_i]\right] \quad (1)$$

and the change in the total particle concentration, $$\sum_i [P_j]$$

is:

$$d/dt \sum_j [P_j] = -k/2 \left(\sum_j [P_j]\right)^2 \quad (2)$$

For an initial monomer (vesicle) concentration, [$P_o$], at t=0, Eqn. 3 has the solution:

$$\sum_j [P_j] = [P_o]/1 + t/\tau \quad (3)$$

in which $\tau=2/k[P_o]$. The mean aggregation number, M, diverges for long times, resulting in flocculation of the colloidal particles:

$$M = [P_o]/\sum_j [P_j] = 1 + t/\tau \quad (4)$$

The diffusion limited rate constant, $k_{ij}$, is given by the mutual diffusion of the particles toward each other: $k_{ij} = 2k_BT/3\eta(1/R_i+1/R_j)(R_i+R_j)$. For the limiting case of $R_i=R_j$, $k_{ij}=k=8k_BT/3\eta=8\times10^9$ liter/mol-sec, in which $k_B$ is Boltzman's constant, T is absolute temperature, and η is the solvent viscosity. For ligand-receptor induced aggregation, a much lower rate constant than diffusion limited is expected due to the steric requirements of the ligand-receptor bond.

Self-Limiting Aggregation

However, these expressions do not describe aggregation caused by cross-linking a limited number of reactive sites on the colloid surfaces. Biotin-lipids on different vesicles must be crosslinked by streptavidin to induce aggregation. If $\theta$ is the average fraction of biotin-lipids bound to streptavidin, a vesicle with $\theta>0$ must contact a vesicle with free biotin-lipid, $(1-\theta)>0$, in order for the vesicles to bind. The new expression for the change of total particle concentration is (See Eqns. 3,4):

$$d/dt \sum_j [P_j] = -k/2(\theta(1-\theta))\left(\sum_j [P_j]\right)^2 \quad (5)$$

As $\theta$ goes from zero to one, the rate of aggregation goes through a maximum, then decreases and eventually stops, giving a finite number of aggregates:

$$\sum_j [P_j] = [P_o]/1 + \left[\left(\int_0^t \theta(1-\theta)dt\right)/\tau\right] \quad (6)$$

with a finite aggregate size, M:

$$M = 1 + \left[\left(\int_0^\infty \theta(1-\theta)dt\right)/\tau\right] \quad (7)$$

again, $\tau=2/k[P_o]$. The average particle size depends on the time evolution of the bound biotin fraction, $\theta$, which in turn is coupled to the size distribution, $[P_j]$.

Each different size aggregate will likely have a different fraction of biotin lipid coupled to streptavidin, $\theta_j$. If all the $\theta_j$ are set equal (in the same level of approximation as the original Smolukowski equation) the equations are greatly simplified and an analytical solution is possible.

However, it is possible to write a simplified equation for $\theta$ that reflects the initial competition for biotin sites on the unaggregated vesicles, and thereby decouple the expressions for $[P_j]$ and $\theta$. The first term in Eqn. 8 is a simple binary expression for reaction of the biotin sites with streptavidin in solution.

Diffusion and reaction of biotin-lipid with a biotin-lipid attached to streptavidin on a given vesicle also leads to an increase in $\theta$. Biotin-lipid and/or biotin-lipid attached to a streptavidin will also diffuse towards existing contact sites between vesicles. At these contact sites, multiple bonds between a vesicle pair can form, leading to a depletion of free biotin (D. Leckband et al., 1995). In Eqn. 8, these effects have the same form as the second term of Eqn. 8, with $k_2$ being replaced by an effective rate constant that reflects all three possible effects. As $k_2$ increases relative to $k_1$, $\delta$ decreases relative to R (Eqn. 10), and $\theta$->1 faster (Eqn. 11). If the vesicle suspension is sufficiently dilute, complete aggregation does not occur for any value of R, and there is no threshold. For our experiments, this occurred for vesicle concentrations $\leq 1$ mg/ml.

The second term is the crosslinking of a streptavidin occupied site on one vesicle with a free biotin site on a second vesicle:

$$n[P_o]\frac{d\theta}{dt} = k_1 n[P_o](1-\theta)N_s + k_2(n[P_o])^2\theta(1-\theta) \quad (8)$$

n is the number of exposed biotin sites per vesicle; the vesicles are at an initial concentration of $[P_o]$. Hence, $n[P_o]$ is the total biotin-lipid concentration exposed on the surface of the vesicles.

Titration of vesicles incorporating 0.16 mol % of biotin-X DHPE with fluorescent BODIPY-labeled avidin or streptavidin (Molecular Probes, Eugene, Oreg.) showed that the fluorescence intensity increased linearly up to a streptavidin to total biotin-lipid mole ratio between 1:8 and 1:9 at which the fluorescence saturated. As streptavidin has 4 binding sites per molecule, this shows that roughly one half of the total biotin-lipids were exposed on the outside of the vesicle. This is consistent with the expected complete miscibility of the biotin-X DHPE with the vesicle phospholipids.

$N_s$ is the concentration of streptavidin in solution:

$$N_s = N_{s,o} - \beta n[P_o]\theta \quad (9)$$

$N_{s,o}$ is the initial streptavidin concentration and $\beta$ is ratio of streptavidin to bound biotin. $\beta$ varies from 1, which corresponds to only one of the binding sites of streptavidin being full, to ¼, which corresponds to all four streptavidin sites being bound to biotin: $¼ \leq \beta \leq 1$. To decouple the equations, it is necessary to make $\beta$ constant.

$\beta$ must start our equal to 1, then decrease to a lower value that likely depends on the streptavidin to biotin ratio. However, good agreement with the fluorescence data. (FIG. 5) is obtained with $\delta$ treated as a fitting parameter, suggesting that $\beta$ approaches a steady state value.

Inserting Eqn. 9 into Eqn. 8, we have, with $R=N_{s,o}/n[P_o]$ as the initial ratio of streptavidin to exposed biotin-lipids:

$$\frac{d\theta}{dt} = n[P_o]k_1(R - \delta\theta)(1-\theta) \quad (10)$$

$$\delta = \beta - \frac{k_2}{k_1}$$

The solution for $\theta$ has the following form:

$$\theta = \frac{\exp\left[\left(1-\frac{\delta}{R}\right)\frac{t}{\tau_1}\right] - 1}{\exp\left[\left(1-\frac{\delta}{R}\right)\frac{t}{\tau_1}\right] - \frac{\delta}{R}} \quad (11)$$

$\tau_1=1/k_1 N_{s,o}$, the time constant for streptavidin addition to biotin-lipids. For $\delta/R<1$, for long times (t->$\infty$), $\theta$->1 and the outer vesicle surface is saturated by streptavidin. For $\delta/R>1$, $\theta$->$R/\delta$, and there are always unreacted biotin-lipids on the vesicle surface. Inserting Eqn. 11 into Eqn. 7, for $\delta/R<1$, gives the mean aggregate size at equilibrium:

$$M = 1 + \frac{\tau_1}{\tau}\left(\frac{R}{\delta}\right)^2\left[-\left(\frac{\delta}{R}\right) - \ln\left(1 - \frac{\delta}{R}\right)\right] \quad (12)$$

M diverges for $\delta/R \geq 1$. Eqn 12 gives a very good representation of the DLS data in FIG. 7. From FIG. 6, the extent of aggregation is independent of vesicle and streptavidin concentration, and the critical value of R when the aggregate size diverges (corresponding to $\delta/R=1$ in Eqn. 12), is $R_{crit} \approx 0.3 = \delta_{crit}$.

Diffusion and reaction of biotin-lipid with a biotin-lipid attached to streptavidin on a given vesicle also leads to an increase in $\theta$. Biotin-lipid and/or biotin-lipid attached to a streptavidin will also diffuse towards existing contact sites between vesicles. At these contact sites, multiple bonds between a vesicle pair can form, leading to a depletion of free biotin (D. Leckband et al., 1995). In Eqn. 8, these effects have the same form as the second term of Eqn. 8, with $k_2$ being replaced by an effective rate constant that reflects all three possible effects. As $k_2$ increases relative to $k_1$, $\delta$ decreases relative to R (Eqn. 10), and $\theta$->1 faster (Eqn. 11). If the vesicle suspension is sufficiently dilute, complete aggregation does not occur for any value of R, and there is no threshold. For our experiments, this occurred for vesicle concentrations $\leq 1$ mg/ml (D. A. Noppl-Simson et al., 1996).

The model can be further evaluated by monitoring the time dependence of the fluorescence of BODIPY-labeled streptavidin as it binds to the biotin-lipids. The fluorescence of the labeled streptavidin is linearly proportional to the number of biotins bound to the streptavidin; hence, this is a direct measure of θ, the average fraction of bound biotin-lipids (N. Emans et al., 1995). The fluorescence intensity as a function of time was measured for a fixed BODIPY-labeled streptavidin concentration ($N_{s,o}$ constant in Eqns. 10–12) when different concentrations of 0.1 micron vesicles of DLPC vesicles incorporating 0.16 mole % of biotin-X DHPC were added and allowed to aggregate. The fit of this data to Eqn. 12 for all of the ratios was surprisingly good considering the limitation of the model. Averaging from the fits, $\tau_1 = 1/k_1 N_{s,o}$, which should be constant between the experiments, is ≈700±100 sec; hence $k_1 \approx 4 \times 10^4$ liter/mol-sec. The diffusion limited rate constant, $k_{ij}$, is given by the mutual diffusion of the particles toward each other: $k_{ij} = 2k_B T/3\eta (1/R_i + 1/R_j)(R_i + R_j)$. For the limiting case of $R_i = R_j$, $k_{ij} = k = 8k_B T/3\eta 8 \times 10^9$ liter/mol-sec, in which $k_B$ is Boltzman's constant, T is absolute temperature, and η is the solvent viscosity. For ligand-receptor induced aggregation, a much lower rate constant than diffusion limited is expected due to the steric requirements of the ligand-receptor bond.

The second parameter, δ, increases as R increases, from about 0.2 at R=0.125 to about 0.3 for R=0.5 to nearly 1 when R=4, but more slowly than R, leading to the crossover between complete flocculation (δ/R>1) to self-limited aggregation (δ/R<1). The increasing value of δ suggests that the average number of streptavidins per bound biotin-lipids, β, in Eqn. 11, increases as R increases, which is consistent with saturation of the vesicle surfaces with streptavidin. The competition for the biotin-lipids at the vesicle surface appears to be the cause of the percolation-like behavior.

To summarize, the extent of ligand-receptor induced vesicle aggregation can be controlled by varying the ratio of soluble receptor to surface-bound ligands. Aggregation exhibits a dramatic change with this ratio—below a critical value, aggregation is self-limiting, the aggregation numbers are finite, and the aggregates remain suspended in solution. Above this critical value, aggregation is complete and the aggregates grow indefinitely and flocculate. A biological system could be controlled to exist near this percolation threshold so that only small perturbations would cause the system to crossover. The threshold could also be crossed by altering the number of binding sites on the receptor, or by altering the long-range forces between the ligands and receptors (D. Leckband, 1995; D. E. Leckband et al., 1994; D. Leckband et al., 1995), between the receptors and vesicles, or between the vesicles themselves (S. A. Walker et al., 1997). This type of reaction induced aggregation could also be generalized to other colloidal systems by incorporating a competitive cross-linking reaction at the colloid surface and would be a useful new way to controllably alter the size distribution of a colloidal dispersion.

REFERENCES

S. A. Walker, Kennedy, M. T. and Zasadzinski, J. A. Encapsulation of bilayer vesicles by self-assembly. *Nature*, 387, 61–64 (1997).

T. H. Whitesides and Ross, D. S. Experimental and theoretical analysis of the limited coalescence process: stepwise limited coalescence. *J. Colloid and Interface Science*, 169, 48–59 (1995).

T. M. Allen, Hansen, C. B. and Lopes de Menezes, D. E. Pharmacokinetics of long-circulating liposomes. *Advanced Drug Delivery Reviews*, 16, 267–284 (1995).

T. M. Allen. Liposomal drug delivery. *Current Opinion in Colloid and Interface Science*, 1, 645–651 (1996).

D. D. Lasic, *Liposomes: From Physics to Applications*, (Elsevier, Amsterdam (1993)., 1993), D. D. Lasic and Papahadjopoulos, D. Liposomes and biopolymers in drug and gene delivery. *Current Opinion in Solid State and Materials Science*, 1, 392–400 (1996).

S. Chiruvolu, Walker, S., Leckband, D., Israelachvili, J. and Zasadzinski, J. Higher order Self-Assembly of Vesicles by Ligand-Receptor Interactions. *Science*, 264, 1753–1756 (1994).

J. A. Zasadzinski and Bailey, S. M. Applications of Freeze-Fracture Replication to Problems in Materials and Colloid Science. *J. Electron Microsc. Technique*, 13, 309–334 (1989).

H. C. Loughrey, Wong, K. F., Choi, L. S., Cullis, P. R. and Bally, M. B. Protein-liposome conjugates with defined size distributions. *Biochim. Biophys. Acta*, 1028, 73–81 (1990).

D. F. Evans and Wennerstrom, H., *The Colloidal Domain*, (VCH Publishers, New York, 1994), D. A. Noppl-Simson and Needham, D. Avidin-biotin interactions at vesicle surfaces—adsorption and binding, cross-bridge formation, and lateral interactions. *Biophysical Journal*, 70, 1391–1401 (1996).

N. Emans, Biwersi, J. and Verkman, A. S. Imaging of endosome fusion in BHK fibroblasts based on a novel fluorimetric avidin-biotin binding assay. *Biophysical Journal*, 69, 716–728 (1995).

D. Leckband. The Surface Forces Apparatus—a tool for probing molecular protein interactions. *Nature*, 376, 617–618 (1995).

D. E. Leckband, Schmitt, F. -J., Isrealachvili, J. N. and Knoll, W. Direct force measurements of specific and non-specific protein interactions. *Biochemistry*, 33, 4611–4624 (1994).

D. Leckband, Muller, W., Schmitt, F. -J. and Ringsdorf, H. Molecular Mechanisms Determining the Strength of Receptor-Mediated Intermembrane Adhesion. *Biophys. J.*, 69, 1162–1169 (1995).

S. A. Walker and Zasadzinski, J. A. Electrostatic control of spontaneous vesicle aggregation. *Langmuir*, 13, 5076–5081 (1997).

What is claimed is:

1. A composition comprising a bilayer structure and multiple containment units, the bilayer structure encapsulating the multiple containment units and which outer bilayer structure is generated from cochleated cylinders and is distinct from the multiple containment units.

2. The composition of claim 1, wherein the containment units are aggregated within the bilayer structure.

3. The composition of claim 1, wherein the multiple containment units include a therapeutic agent.

4. The composition of claim 1, wherein the multiple containment units include a diagnostic agent.

5. A vesosome having a bilayer structure and multiple vesicles, the bilayer structure encapsulating the multiple vesicles and which outer bilayer structure is generated from cochleated cylinders and is distinct from the multiple vesicles.

6. The vesosome of claim 5, wherein the vesicles are aggregated within the bilayer structure.

7. The vesosome of claim 5, wherein the multiple vesicles are of different size.

8. The vesosome of claim 5, wherein the multiple vesicles are of the same size.

9. The vesosome of claim 5, wherein the multiple vesicles include a therapeutic agent.

10. The vesosome of claim 5, wherein the multiple vesicles include a diagnostic agent.

11. A method for encapsulating multiple containment units within a bilayer structure comprising:

a. obtaining aggregated multiple containment units in a solution;

b. adding cochleated cylinders to the solution; and c. mixing the aggregated multiple containment units of step (a) and the cochleated cylinders of step (b) in the solution under suitable conditions so that the cochleated cylinders transform to create the bilayer structure that encapsulates the aggregated multiple containment units.

12. A method for delivering a therapeutic agent to a target site that comprises introducing the vesosome of claim 9 to the target site under conditions so that the therapeutic agent is released therefrom.

13. The method of claim 12, wherein the vesosome is introduced by intramuscular injection, intravenous injection, oral administration, pulmonary adsorption, rectal, nasal, oral, ocular, vaginal, or uretheral administration, subcutaneous injection, sublingual administration, or topical application.

14. A method for delivering a therapeutic agent to a target site that comprises introducing the composition of claim 3 to the target site under conditions so that the therapeutic agent is released therefrom.

15. The method of claim 14, wherein the composition is introduced by intramuscular injection, intravenous injection, oral administration, pulmonary adsorption, rectal, nasal, oral, ocular, vaginal, or uretheral administration, subcutaneous injection, sublingual administration, or topical application.

16. The method of claim 12 or 14, wherein the therapeutic agent is a drug acting at synaptic and neuroeffector junctional sites.

17. The method of claim 16, wherein the drug is selected from a group consisting of a neurohumoral transmitter, a cholinergic agonist, an anticholinesterase agent, an antimuscarinic drug, an agent acting at the neuromuscular junction and autonomic ganglia, a catecholamine, a sympathomimetic drug, and an adrenergic receptor antagonist.

18. The method of claim 12 or 14, wherein the therapeutic agent is a drug acting on the CNS.

19. The method of claim 18, wherein the drug is selected from a group consisting of an antipsychotic drug, a neuroleptic drug, tricyclic antidepressants, monoamine oxidase inhibitors, lithium salts, and benzodiazepines.

20. The method of claim 12 or 14, wherein the therapeutic agent is a drug which reduces inflammation.

21. The method of claim 20, wherein the drug is selected from a group consisting of antagonists of histamine, bradykinin, 5-hydroxytryptamine; lipid-derived autacoids; methylxanthines, cromolyn sodium; analgesic-antipyretics.

22. The method of claim 12 or 14, wherein the therapeutic agent is a drug which affects renal function and electrolyte metabolism.

23. The method of claim 22, wherein the drug is selected from a group consisting of diuretics and inhibitors of tubular transport of organic compounds.

24. The method of claim 12 or 14, wherein the therapeutic agent is a drug which affects cardiovascular function.

25. The method of claim 24, wherein the drug is selected from a group consisting of renin and angiotensin; organic nitrates, calcium-channel blockers and beta-adrenergic antagonists; antihypertensive agents, digitalis, antiarrhythmic drugs, and drugs used in the treatment of hyperlipoproteinemias.

26. The composition of claim 2, wherein the aggregation of the containment units is by ligand-receptor interaction.

27. The composition of claim 6, wherein the aggregation of the vesicles is by ligand-receptor interaction.

* * * * *